(12) United States Patent
Jussel et al.

(10) Patent No.: US 10,041,734 B2
(45) Date of Patent: Aug. 7, 2018

(54) DENTAL FURNACE

(75) Inventors: Rudolf Jussel, Feldkirch-Gisingen (AT); Gottfried Rohner, Altstätten (CH)

(73) Assignee: Ivoclar Vivadent AG, Schaan (LI)

( * ) Notice: Subject to any disclaimer, the term of this patent is extended or adjusted under 35 U.S.C. 154(b) by 667 days.

(21) Appl. No.: 13/555,446

(22) Filed: Jul. 23, 2012

(65) Prior Publication Data

US 2013/0029281 A1    Jan. 31, 2013

(30) Foreign Application Priority Data

Jul. 25, 2011   (EP) ..................................... 11175231

(51) Int. Cl.
| | |
|---|---|
| *F27D 21/04* | (2006.01) |
| *F27B 17/02* | (2006.01) |
| *A61C 13/20* | (2006.01) |
| *F27D 21/00* | (2006.01) |

(52) U.S. Cl.
CPC ............ *F27B 17/025* (2013.01); *A61C 13/20* (2013.01); *F27D 21/00* (2013.01)

(58) Field of Classification Search
USPC ....................................................... 432/32, 1
See application file for complete search history.

(56) References Cited

U.S. PATENT DOCUMENTS

| | | | | |
|---|---|---|---|---|
| 6,484,791 | B1 * | 11/2002 | Vidal ............................ | 164/113 |
| 7,156,637 | B1 * | 1/2007 | Kutsch et al. ................ | 425/178 |
| 7,995,195 | B2 | 8/2011 | Feichtinger et al. | |
| 8,232,506 | B2 | 7/2012 | Jussel | |
| 2002/0062117 | A1 | 5/2002 | Raufman et al. | |
| 2003/0000275 | A1 * | 1/2003 | Spence ................ | B21D 26/055 72/342.1 |
| 2003/0234095 | A1 | 12/2003 | Usui | |
| 2008/0096148 | A1 | 4/2008 | Jussel | |
| 2008/0099939 | A1 | 5/2008 | Jussel et al. | |
| 2008/0237211 | A1 * | 10/2008 | Jussel .................... | A61C 13/20 219/390 |
| 2009/0136900 | A1 * | 5/2009 | Gritsch .................. | A61C 13/20 433/201.1 |

(Continued)

FOREIGN PATENT DOCUMENTS

| | | | | |
|---|---|---|---|---|
| DE | 102004049888 A1 | 4/2006 | | |
| EP | 2026054 A2 * | 2/2009 | ............ | F27B 17/025 |

(Continued)

OTHER PUBLICATIONS

EP2026054A2—machine translation.*

(Continued)

*Primary Examiner* — Nathaniel Herzfeld
(74) *Attorney, Agent, or Firm* — Ann M. Knab; Thad McMurray

(57) ABSTRACT

A dental furnace (10), with a furnace head (including firing space 16) and a firing space bottom (12) is provided which is suited to accommodate a dental restoration part (40). At least one optical sensor (22) is positioned at the dental furnace (10) or in its vicinity, which sensor comprises an output port (26) which is connected to an evaluation device for evaluating the dental restoration part (40) and/or a muffle (14) and/or a press plunger (52) and/or a firing-charge carrier as far as its dimensions and/or its shape and/or its position are concerned.

17 Claims, 10 Drawing Sheets

(56) References Cited

U.S. PATENT DOCUMENTS

| | | | |
|---|---|---|---|
| 2009/0155736 A1* | 6/2009 | Vekoerrer et al. | 433/34 |
| 2009/0180118 A1 | 7/2009 | Feichtinger et al. | |
| 2009/0246739 A1 | 10/2009 | Jussel et al. | |
| 2014/0113237 A1* | 4/2014 | Rohner et al. | 431/1 |

FOREIGN PATENT DOCUMENTS

| | | | | |
|---|---|---|---|---|
| GB | 2390674 A | * | 1/2004 | F23N 5/082 |
| JP | S60200130 A | | 10/1985 | |
| JP | 2002062117 A | * | 2/2002 | |
| JP | 2003261964 A | | 9/2003 | |
| RU | 2063727 C1 | | 7/1996 | |
| WO | 2005116557 A1 | | 12/2005 | |

OTHER PUBLICATIONS

EP2026054A2—claims.*
JP2002062117A—machine translation.*
Wikipedia, "Thermographic camera," encyclopedia article, https://en.wikipedia.org/wiki/Thermographic_camera, Retrieved Apr. 3, 2017.
Wikipedia, "Infrared," encyclopedia article, https://en.wikipedia.org/wiki/Infrared, Retrieved Apr. 3, 2017.

* cited by examiner

DENTAL FURNACE

CROSS-REFERENCE TO RELATED APPLICATIONS

This application claims the benefit of European Patent Application No. 11175231.7 filed Jul. 25, 2011, which is hereby incorporated by reference in its entirety.

TECHNICAL FIELD

The present invention relates generally to a dental furnace and a process for operating a dental furnace.

BACKGROUND

Dental furnaces for firing dental restoration parts have been known for a long time. In dental furnaces, a dental restoration part or a number of dental restoration parts are subjected to a firing process or sintering process, in accordance with a precisely prescribed temperature profile.

The quality of the dental restoration parts produced depends essentially on the intended parameters which are optimally adapted for the dental restoration material and are exactly adhered to during the firing process. This comprises not only the temperature profile to be adhered to, not inside the furnace but at the dental restoration part itself, but also the existing vacuum conditions during the firing cycle.

Such dental restoration parts comprise dental restoration parts to be manufactured of plastics, of metal, of composites, and, in particular, also of ceramics.

Ceramic dental restoration parts are often produced in what is referred to as muffles, in which hollow molds correspond to the precise shape of the future dental restoration part as negative impressions. Such patterns are made of wax or similar materials as positive patterns, are mounted on a common basis via what is referred to as waxing sprues, and are then cast out with a material which cures true to shape and which in most cases contains plaster.

After the wax has been melted out, hollow spaces are available, with the waxing sprues being connected with one another via a common press channel which in most cases is of cylindrical shape, and ending at the hollow spaces in which the dental restoration parts are to be produced.

When a dental restoration part is to be pressed, a green body or press blank is introduced into the press channel and is subjected to pressure with the help of a molding plug. During the process of heating to reach the sintering temperature of the ceramic material of which the press blank consists, the press blank begins to take a plastic state and is introduced into the hollow shaping spaces for the production of dental restoration parts by means of pressure exerted on the molding plug.

This process has been known for a long time, but lately attempts have been made to improve the throughput of dental press furnaces, for instance by pressing more or larger dental restoration parts together in one muffle.

Larger hollow shaping spaces or a larger number of shaping spaces, however, lead to a certain weakening of the muffle. For this reason, the furnace parameters for preventing the formation of cracks in the muffle or other damage of the dental restoration parts must be adhered to even more precisely.

It has already been suggested as well, as can be seen from DE 10 2006 050 830 A1 and corresponding US Published Application No. 2008099939, which is hereby incorporated by reference, to monitor whether the muffle which is subject to pressure exhibits a crack during the pressing process. This evaluation, however, can basically be done after the fact, and it would be desirable to safely prevent cracks in the muffle already in advance.

In order to guarantee this with a certain safety margin, the muffles produced are subjected to a prescribed press force to be set by the user, which force is clearly lower than the press force at which cracks might appear.

A reduced press force, on the other hand, offers the risk of the dental restoration parts having to remain in the firing furnace for too long, so that the hollow shaping spaces are completely filled, and also the risk of the user by accident interrupting the pressing process because the user assumes that the pressing process has been completed, for instance when the molding plug does not move further downwards. This can happen, in particular, when there is comparably high friction inside the shank. A dental furnace operated at reduced press force is more vulnerable for such friction faults in comparison to a dental press furnace operated at high press force.

Another quality problem is that parameters are by accident set wrongly for the firing process and/or the pressing process to be carried out. This can result in the press force being set too high or too low, or in the firing temperature being set too high or too low. The dental restoration part produced will then be of minor quality, which in many cases will go unnoticed because it will not recognizable in the finished dental restoration part. Damage will in this case occur only after the part has been used inside the mouth of the patient, in different cases often for years, for which then the dentist or the producer of the dental restoration material will be blamed, even if it was indeed the dental technician operating the press furnace who made an error.

In large dental laboratories, the work process is often split, such that certain dental technicians do only certain jobs with given parameters, which to put into practice will quite possibly also be feasible at the same firing furnaces which in most cases cover a rather large range in accordance with the client's wishes. In order to limit the range of parameters for the necessary dental technical work, it has already been suggested to draw up what is referred to as user profiles which make it necessary for the respective user to register with the dental furnace before firing curves and press curves available for selection within his range are presented to him. For a correct assignment, however, it is vital that the user also logs off when he has finished his job at the firing furnace concerned, which is thought to be awkward, such that it is to be feared that another user will accidentally carry out some wrong operation, assuming that the dental furnace concerned is presenting him the "correct" firing curves and press curves for selection.

SUMMARY

The invention has the task of providing a dental furnace with the help of which work in a dental laboratory is improved even with complex applications and high expectations of the users as to quality, without making the operation of the dental furnaces any more complicated than is relevant in practice.

This task is fulfilled in accordance with the invention by the attached claims, which are herein incorporated by reference.

In accordance with an embodiment of the present invention, it is particularly favorable to incorporate an optical sensor in order to detect certain conditions relevant for the operation of the dental furnace and control the dental furnace accordingly based on the detection result. Here, the expression "optical sensor" shall be understood to be an alignment of identical or essentially identical elements sensitive to radiation.

In case of a one-dimension alignment, such an optical sensor can also be composed of a number of individual sensor elements which can for example also include infrared sensors, in case of an alignment of the individual sensor elements in two dimensions, in contrast, picture recording and imaging in these two dimensions is possible as well, as can for instance be put into practice with the help of a CCD unit of a digital camera. If realized as a CCD unit, it is also possible in a favorable embodiment to realize what is referred to as a thermal imaging camera which has its maximum sensitivity in the infrared range from 3000 nm to 15,000 nm, or as a digital camera for the range of visible light, i.e. between 300 nm and 750 nm.

In accordance with an embodiment of the present invention, it is particularly favorable that non-contact measurement is possible thanks to the provision of the dental furnace, in accordance with an embodiment of the present invention, with an optical sensor. For instance, the size of a dental restoration part, a press plunger, a muffle or a firing charge carrier can be measured, also their shapes, respectively, and their positions, respectively, as well. Here too the optical sensor, which can very well reach into the range of infrared in its measuring range, makes possible a measurement of the temperature, and it is also possible to transmit the measuring result over larger distances.

Mechanical deformations or other deviations do not have any influence on the measurement.

With the help of the monitoring provided in an advantageous embodiment, control of the dental furnace is possible by the user via a display device or in any other suitable form. When the optical sensor is directed towards the dental restoration part or the muffle, the control device also recognizes without any problem when the muffle or the dental restoration part is introduced and removed.

This is also true for firing charge carriers, and it is possible, for instance, to detect, in accordance with color, whether the correct firing charge carrier has been introduced.

Monitoring is not restricted to the muffle. It is also possible, for example, to monitor the position of an aluminum-oxide plunger or a molding plug inside the muffle. As is known, the latter must be positioned deeper inside the muffle after the pressing process, which can be detected via position detection.

In a first embodiment of the solution in accordance with an embodiment of the present invention, it is intended to drive a control device for the dental furnace with the help of the optical sensor. The control device then triggers the desired function depending on the image recorded or other signal output as is transmitted by the optical sensor.

Thus it is possible, with a correspondingly high-resolution realization of the CCD unit, to recognize the object to be treated. This can for example be a dental restoration part to be fired, and the control device then triggers the related program. It is also possible to realize the corresponding recognition in a supported fashion, i.e., for instance, with the help of bar codes on the packing of the product. However, it is preferred for the optical sensor to recognize the object directly and trigger the desired program function.

For example, it is possible to recognize the size of a dental restoration part to be fired by means of image recognition and to determine the corresponding parameters.

Another possibility is the automatic identification of muffles. Their sizes, lot numbers or the like can be recognized, and furnace control can be adapted in a suitable fashion.

The optical sensor in accordance with an embodiment of the present invention can either be firmly connected with the housing or the lower portion of the dental furnace, or it can be connected with the control device of the dental furnace via a suitable connection, such as, for example, a wireless connection, an electric cable or the like.

In an advantageous embodiment of the invention, the optical sensor is provided as a multiple arrangement of individual light-sensitive elements in a row and specially adapted to recognizing the diameter of a muffle. For this purpose, the arrangement with light-sensitive elements of the optical sensor preferably extends horizontally, corresponding to the vertical positioning direction of a muffle in a dental furnace. It is also possible to introduce a basically known temperature measuring camera and merely evaluate one line of the matrix provided there. Each detection element will then correspond to one pixel. The number of pixels which are hit by optical radiation or thermal radiation from the muffle will then allow conclusions to the diameter of the muffle. The desired precision is already sufficient if the width of a pixel corresponds to a difference in the diameter of, for example, 4 mm.

Based on the measuring result present, the control device is provided with the corresponding information and will drive the furnace in a suitable fashion, for instance by selecting a longer firing cycle for muffles with larger diameters.

In an advantageous embodiment, it is intended to evaluate not only the diameter of the muffle, but also the height of the muffle. For this purpose, a two-dimensional detection of the muffle outlines via the optical sensor is provided. In an alternative embodiment, it is intended to evaluate a pixel line of the CCD unit, as described above, as well as a pixel column of the unit. From the evaluation of the pixel column, the height of the muffle will result here, and from the pixel width the diameter will result.

It is to be understood that the optical sensor takes a given position relative to the muffle. For example, the muffle can be positioned at a given recess in the firing chamber bottom, and the optical sensor can be firmly mounted to the lower portion of the furnace in such a fashion that it is directed towards the muffle.

In an advantageous embodiment, it is intended that the format selection of the optical sensor can be adapted to the requirements. If, for example, in the vertical direction pixel resolution is higher than in the horizontal direction, the picture evaluation of an image standing in an upright position is favorable. If, vice versa, the number of pixels in the horizontal direction is larger than in the vertical direction, a higher resolution is available for an evaluation in the horizontal direction, such that even objects positioned next to each other, such as, for instance, multi-member crowns lying flatly can well be evaluated.

It is possible to enlarge or reduce the size of the image area with the help of zoom optics.

In an advantageous embodiment it is intended that the control device has a comparison device which compares images recorded with images detected by the optical sensor. This also includes, for instance, certain muffle sizes, and also certain sizes of dental restoration parts.

In a preferable embodiment, the evaluation device is connected to a display device with the help of which information about the dimensions and/or the shape and/or the position can be displayed, and/or to a control device for controlling the dental furnace.

In a preferable embodiment, a monitoring device of the dental furnace is connected to the sensor, with the help of which device a temporal change in the dimensions and/or shape and/or position can be detected.

In a preferable embodiment, the sensor comprises a detection area which extends, at least partially, inside the firing space above the firing space bottom of the dental furnace and through which, in particular, the central longitudinal axis of the firing space extends as well.

In a preferable embodiment, the furnace head is removable from the firing space bottom, and can be lifted off the latter, such that the sensor is directed towards a detection area which extends between the firing space bottom and the furnace head in the open state of the furnace.

In a preferable embodiment, the sensor is mounted in such a fashion that it can be swiveled, and is, in particular, attached to the dental furnace in such a fashion that it can be swiveled.

In a preferable embodiment, the sensor is formed to be a picture recording device with the help of which an image of the dental restorations and/or the muffle and/or the press plunger and/or the firing charge carrier can be recorded.

In a preferable embodiment, the sensor is formed to be a picture recording device which evaluates the recorded image line-wise and/or column-wise and determines its dimensions based on the evaluation result in a width extending in a parallel fashion to the firing space bottom or in a height extending in a vertical fashion to the firing space bottom of the dental restoration part and/or the muffle and/or the press plunger and/or the firing charge carrier, in particular, by determining the number of pixels which correspond to the width or height, respectively, of the object recorded, with the number of pixels being realized by a comparison of the pixels corresponding to the object as opposed to the pixels corresponding to the background, based on a pre-set criterion.

In a preferable embodiment, the criterion mentioned is the temperature and/or the brightness and/or the color of the object.

In a preferable embodiment, the sensor detects electromagnetic waves within a range of wavelengths of 380 nm and 18 μm and, in particular, comprises a multitude of sensor elements.

In a preferable embodiment, the optical sensor comprises at least two sensor elements which are positioned at an angle to one another and, in particular, have detection areas which at least partly overlap each other.

In a preferable embodiment, the optical sensor forms part of a light barrier which, in particular, comprises at least two sensor elements as well as at least one transmitter of electromagnetic rays, the presence of which can be detected by the sensor elements.

In a preferable embodiment, the sensor is connected to a control device via which a dental restoration part or a muffle can be detected in view of its size, and wherein the control device determines furnace parameters depending on the size of the dental restoration part, in particular, depending on the width of the muffle thus detected.

In a preferable embodiment of the process In accordance with an embodiment of the present invention, the control comprises a pre-selection of processing programs of the dental furnace after the control device has recognized the object recorded, in particular, the size of a muffle positioned upon the firing space bottom.

In a preferable embodiment, the temperature of the dental restoration part and/or the muffle and/or the press plunger and/or the firing charge carrier can be detected by the sensor, and wherein the control device controls the dental furnace depending on the temperature detected.

BRIEF DESCRIPTION OF THE DRAWINGS

Embodiments of the present invention will be more fully understood and appreciated by the following Detailed Description in conjunction with the accompanying drawings, in which.

DETAILED DESCRIPTION

A dental furnace 10 in accordance with an embodiment of the present invention has a firing space bottom 12 which is intended to take up a muffle 14. For the firing process, the muffle 14 is taken up in a firing space 16 which is depicted schematically and by broken lines in FIG. 1, and which is formed in a furnace hood which is not depicted.

Figure 1:
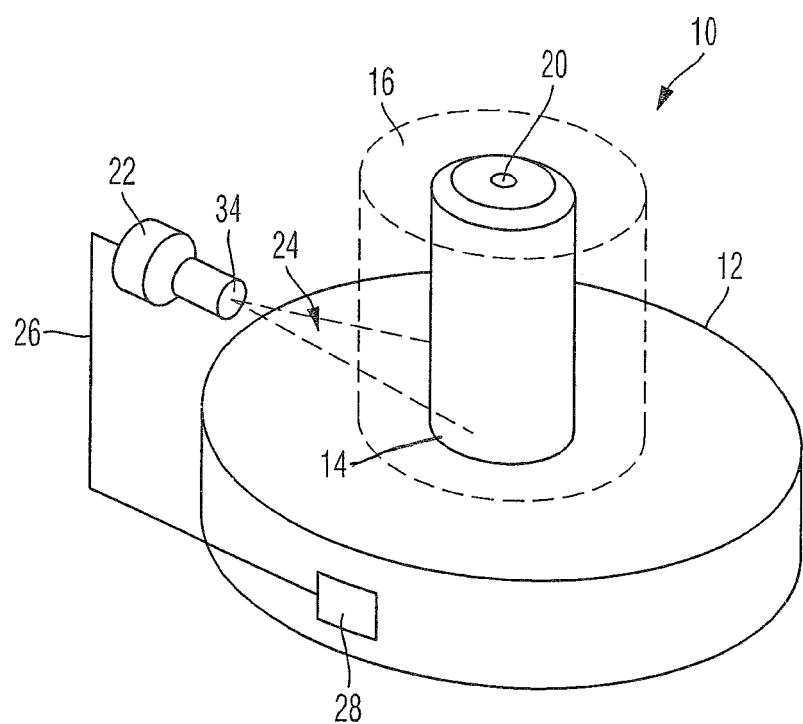
FIG. 1 is a schematic view of an embodiment of a detail of a dental furnace in accordance with the present invention.

In the condition depicted in FIG. 1, the furnace hood (including the firing space 16), however, is lifted such that the muffle 14 is visible.

The muffle 14 is destined to form dental restoration parts. For this purpose, it is provided with a press channel 20 which is intended for taking up a press plunger. Inside the muffle 14, hollow shaping spaces are formed in an also basically known fashion, which hollow spaces determine the dental restoration parts in their shape.

In accordance with an embodiment of the present invention, an optical sensor 22 is positioned laterally with respect to the firing space, however a little above the latter. The optical sensor 22 is directed towards the muffle 14 in the exemplary embodiment depicted, and its detection area 24 covers the maximum possible size of a muffle in the firing space 16. The detection area 24 of the optical sensor 22 is basically cone-shaped for this purpose. The optical sensor 22 thus detects the width of the muffle 14, and in a preferable embodiment also the height of the muffle 14.

The optical sensor is provided with an output port 26 which is connected with a control device 28 for the dental furnace via any connection suitable for this purpose. The control device 28 drives the dental furnace in such a fashion as is optimal for the muffle 14 detected. If, for instance, a larger muffle 14 is detected, the firing cycle will automatically extend, in order to account for the increased heat capacity of the muffle and in order to achieve a constant dental restoration result.

An image recognition means is provided for this purpose inside the control device, which evaluates the image recognized and recorded by the optical sensor and makes the size of the muffle detected the basic evaluation scale.

Even if a muffle size recognition means is provided inside the dental furnace or, to be more precise, above the lower portion of the dental furnace, it is to be understood that in an equivalent fashion, a muffle size recognition means can also be provided outside the lower portion of the dental furnace. In a preferable embodiment of the invention, it is also possible to realize the evaluation both in the position in accordance with FIG. 1 and with respect to other positions not shown. For this purpose, the optical sensor 22 can either be firmly mounted or can be supported separately in front of the dental furnace 10. How this can be realized can be taken schematically from FIG. 3.

Figure 2:
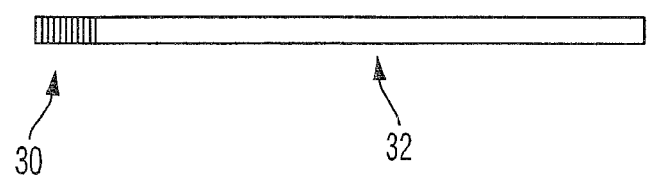
FIG. 2 is a schematic view of a detail of the optical sensor belonging to FIG. 1.

From FIG. 2 the schematic alignment of individual detection elements 30 of the light-sensitive unit of the optical sensor 22 can be taken. As can be seen, a multitude of individual detection elements 30 is aligned one after another, with the minimum necessary resolution—corresponding to the number of individual detection elements, being adaptable to a great extent to the requirements. The light-sensitive unit 32 in accordance with FIG. 2 can also form part of a CCD unit which is provided in the form of a matrix of the optical sensor 22. In this case, merely one line of the CCD matrix is evaluated.

The individual detection elements 30 in accordance with FIG. 2 recognize through an optics element 34 of the optical sensor the width or the diameter of the muffle 14. For this purpose, the exposure of the individual detection elements 30 activated by the muffle 14 differs from that of those not activated. The number of detection elements 30 activated corresponds to the diameter of the muffle and is for which a signal is sent to the control device 28.

Figure 3:
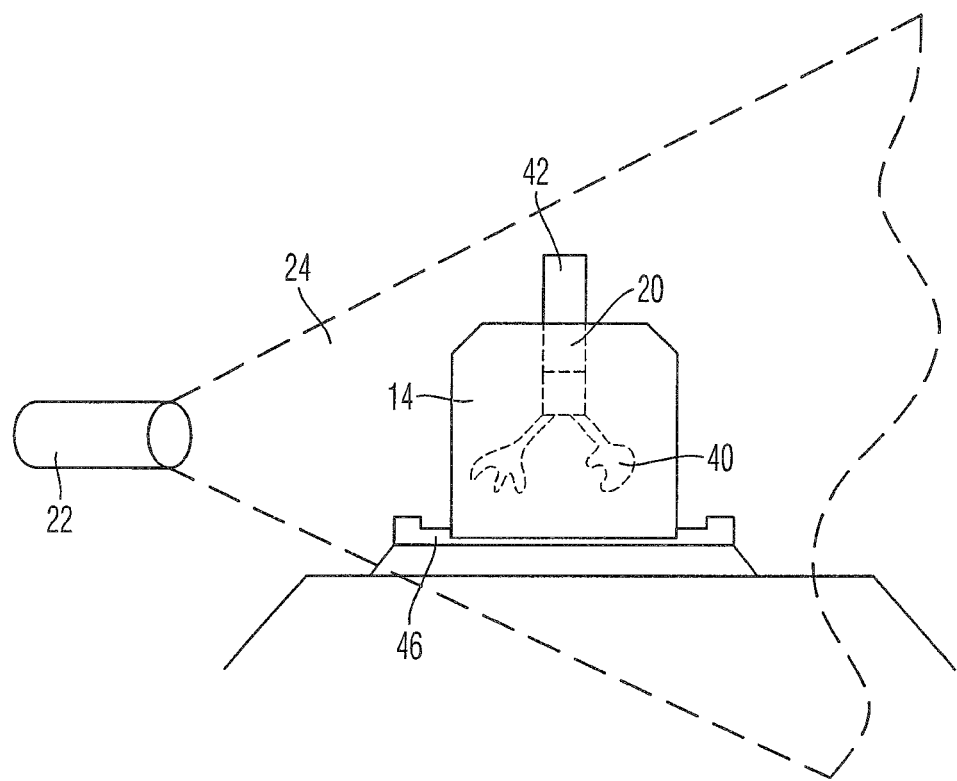
FIG. 3 is a schematic view of another embodiment of a portion of a dental furnace in accordance with the present invention.

From FIG. 3 it can be shown in which fashion a muffle can be detected by the optical sensor 22. The optical sensor 22 is provided with a detection area 24 which essentially extends in a conical shaped manner from the optical sensor 22 towards the front, i.e., in the direction towards the muffle 14. As shown in FIG. 3, a hollow space for a dental restoration part 40 is provided inside the muffle 14, with several hollow spaces being realized in the exemplary embodiments depicted.

A press plunger 42 is also positioned within the detection area 24 and can also be detected by the optical sensor 22. Thus, it is also possible to detect, with the help of the optical sensor 22, to what extent the press plunger 22 has already been pushed inside the muffle 14.

The muffle 14 is adapted to a firing space bottom 12 or 46 in accordance with FIG. 3. The firing space bottom is provided with a recess, for supporting or holding the muffle 14. For supporting or holding muffles of different diameters, a number of recesses is provided in a stepped or graded fashion, which recesses are each adapted to the possible sizes of muffles and with the help of which it is made sure that the muffle is placed in a centered position.

The detection area 24 of the optical sensor 22 extends not only in a vertical direction, but, in particular, also in a horizontal direction. Thus it is also possible to detect the position and also the width of the muffle 14. Thus, if for instance the muffle is positioned too far sideward, i.e., not in a centered position, inside the recess, which could result in faulty pressing, this can also be detected with the help of the optical sensor 22.

Figure 4A:
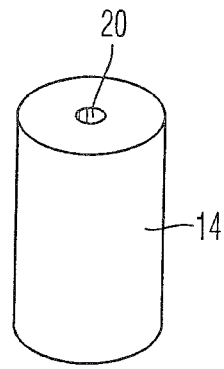
FIG. 4a to FIG. 4f are schematic views of muffles which are destined for an embodiment of the dental furnace in accordance with the present invention.
Figure 4B:
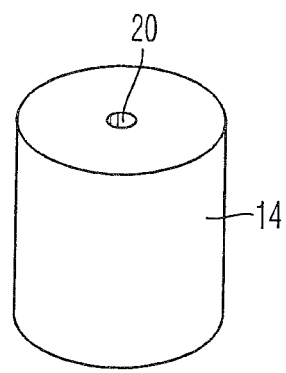

As can be taken from FIGS. 4a to 4f, differently shaped muffles, respectively, can be classified and evaluated in order to select the suitable program for the dental furnace 10. FIG. 4a differs from FIG. 4b in that the muffle in accordance with FIG. 4a has a distinctly smaller diameter, but has the same diameter of the press channel. The thermal capacity of the muffle 14 in accordance with FIG. 4b typically is considerably larger compared to that in accordance with FIG. 4a, and fast heating with a temperature-balancing phase is recommended, during which phase the temperature in the muffle 14 can be balanced.

Figure 4C:
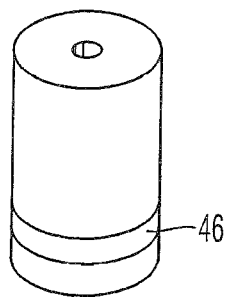

In accordance with FIG. 4c, a muffle is provided which bears a marking ring 46. The marking ring 46 permits, for example, indications as to what dental material is used, such as, for instance, lithium disilicate or zirconium dioxide, and thus significantly influences the press curve.

Figure 4D:
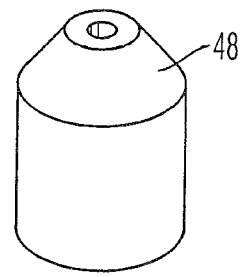
Figure 4E:
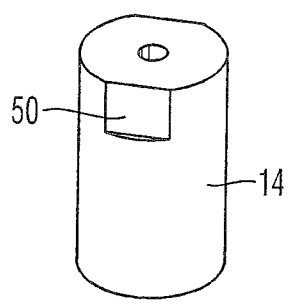
Figure 4F:
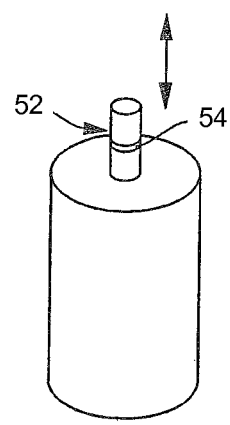

In accordance with FIG. 4d, a muffle with a beveling 48 at its upper end is provided. Such a muffle permits a lifting/pivoting movement even with a firing space whose diameter is only scarcely larger than the outside diameter of the muffle.

A marking 50 of a different type is provided as a flattened portion which differentiates the muffle 14 depicted there from other muffles.

Also, a press plunger 52 which can be introduced into the press channel 20 can be provided with a marking 54 in any suitable fashion, which marking can be detected by the optical sensor 22.

Figure 5:
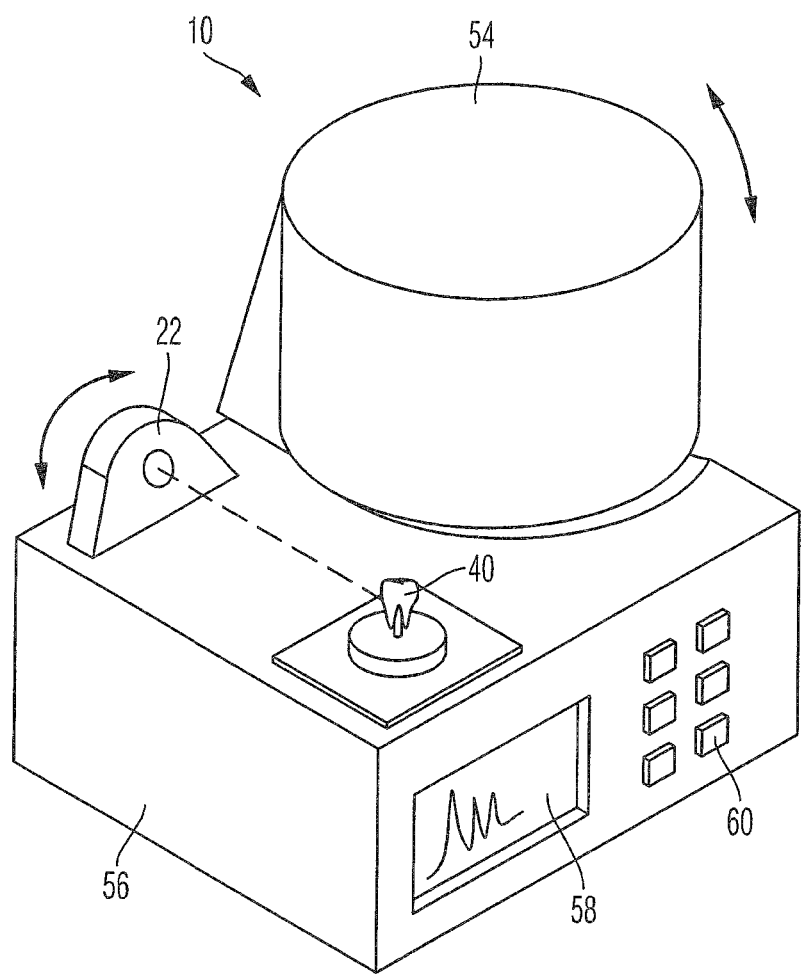
FIG. 5 is another schematically depicted embodiment of a dental furnace in accordance with the present invention.

The dental furnace 10 depicted in FIG. 5 is provided with an optical sensor 22 which is directed towards the dental restoration part 40 which is put next to a furnace hood 54 on a furnace bottom part 56. As can be taken from FIG. 5 schematically, the optical sensor 22 can be swiveled around a vertical axis not depicted, such that it can also be directed towards the firing space when the furnace hood is open and can recognize a dental restoration part 40 or a muffle placed there.

The dental furnace 10 in accordance with FIG. 5 is provided with a display device 58 as well as operation keys 60, and the furnace hood 54 is mounted in such a fashion that it can be swiveled around a horizontal axis or can be lifted.

Figure 6:
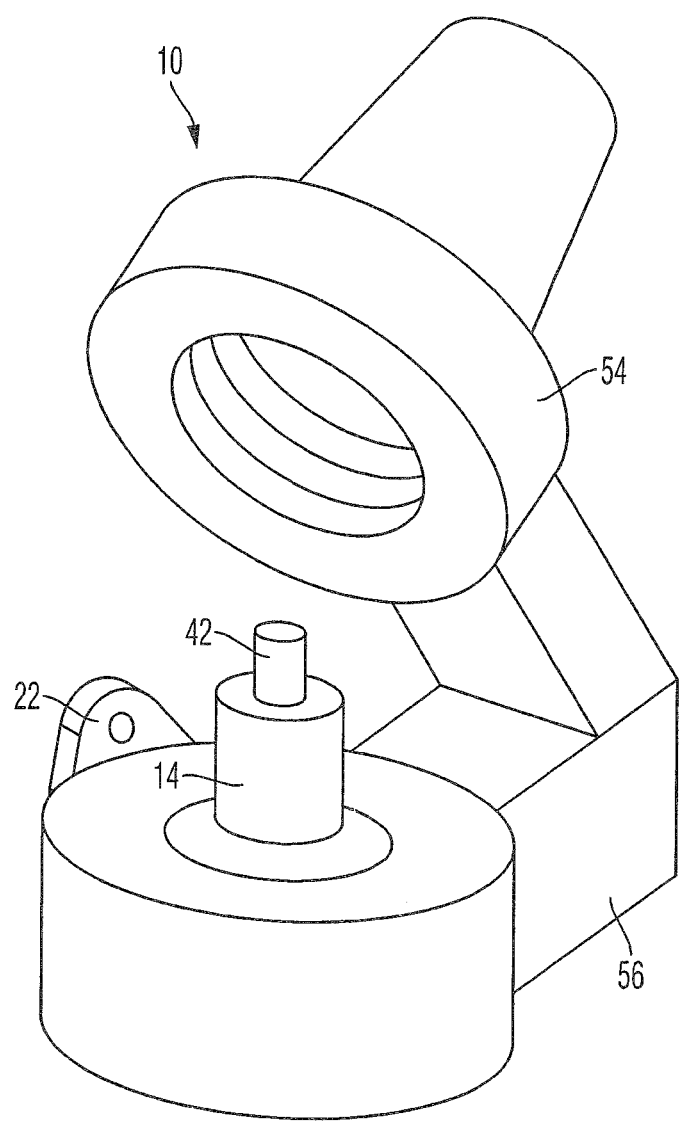
FIG. 6 is another schematically depicted embodiment of a dental furnace in accordance with the present invention, with the furnace hood opened in the depiction.

The embodiment in accordance with FIG. 6 also shows an embodiment of a dental furnace 10 with a furnace hood 54. The furnace hood 54 is formed in such a fashion that it is suitable for the maximum possible size of the muffle 14. The optical sensor 22 is attached laterally to the lower portion 56 of the furnace and is directed towards the muffle 14. The detection area of the optical sensor makes it possible to notice that the muffle 14 does not exceed the admissible size, and also that it is not placed in a position which would collide with the inner side of the furnace hood 54 when the latter is closed.

Figure 7:
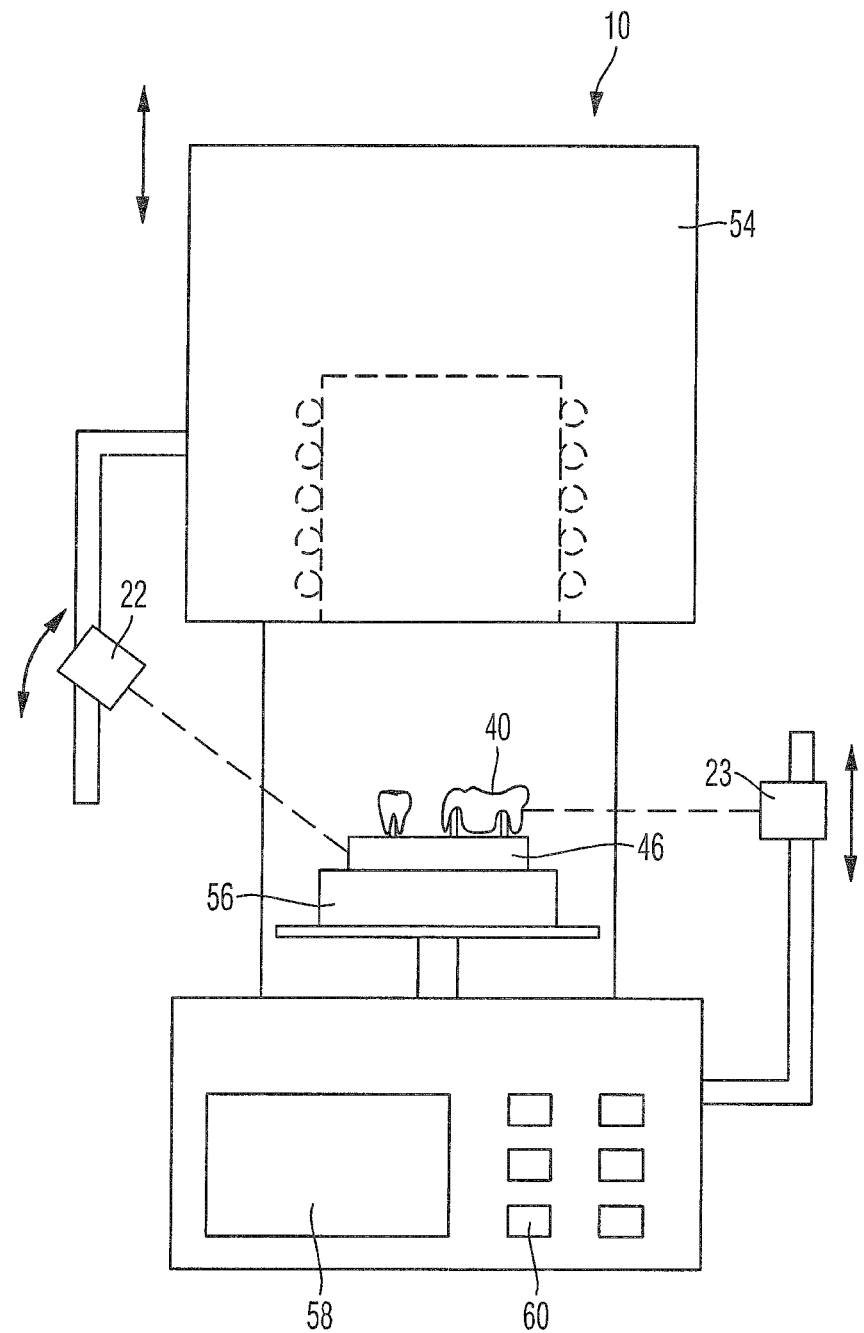
FIG. 7 is another schematically depicted embodiment of a dental furnace in accordance with the present invention.

A modified version of a dental furnace 10 with a vertically lowerable lower portion 56 of the furnace can be taken from FIG. 7. In this embodiment, two optical sensors 22 and 23 are provided which are both directed towards the firing space bottom and a little above the firing space bottom, respectively, in order to be able to detect dental restoration parts 40 positioned there. Here, the optical sensor 23 can be moved in a vertical direction, and the optical sensor 22 can be swiveled, each in order to be able to detect the desired information about the dental restoration parts and their arrangement on the firing space bottom 46 in the best possible fashion.

Figure 8:
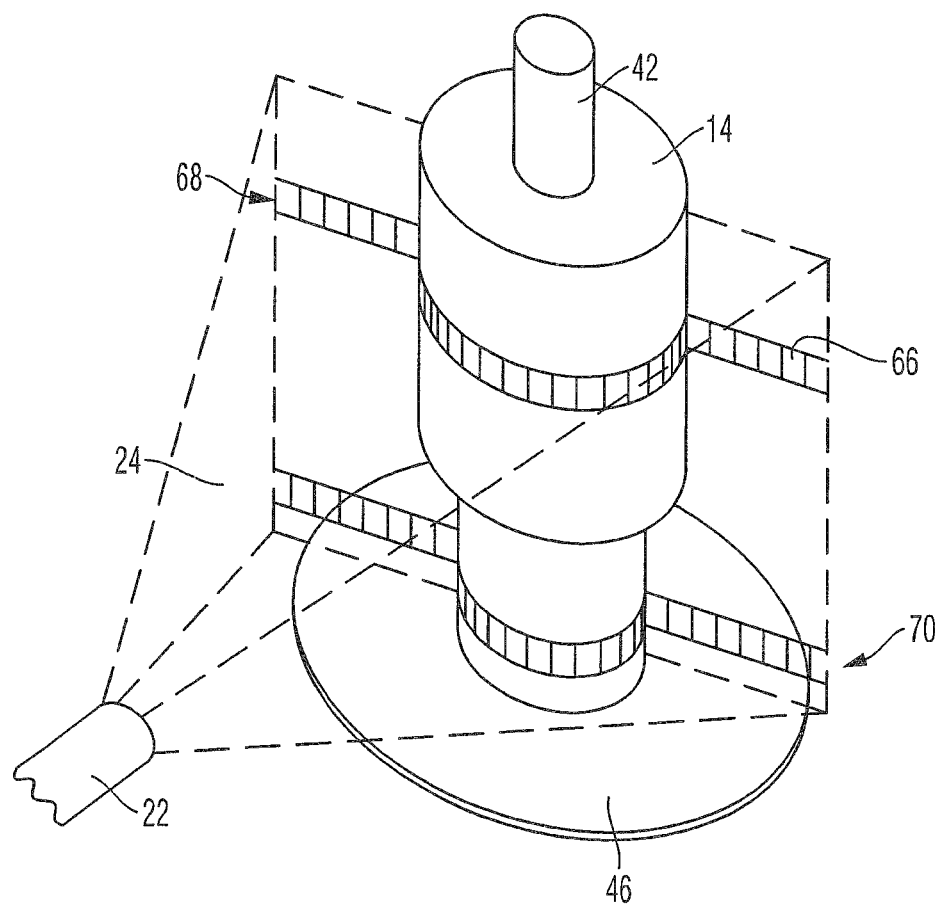
FIG. 8 is a schematic depiction of an optical sensor in accordance with the present invention during operation.

In FIG. 8 it is depicted in which way the detection area 24 of the optical sensor can extend beyond a muffle 14. The optical sensor 22 detects the width of the muffle 14 in a horizontal direction. For this purpose, a multitude of pixels 66 is evaluated, and in the exemplary embodiment depicted this is done at an upper vertical position 68 and at a lower vertical position 70. By comparing the pixel values determined, it is also possible to roughly determine the shape of the muffle 14.

It is to be understood that the optical sensor can be adapted to compare the reflection properties of the muffle 14 with the reflection properties of the background and determine differences. Typically, for instance, a muffle is white, while the background is typically of a different color than white. Thus a differentiation is also possible, even if only the range of visible light is evaluated by the optical sensor 22.

In a modified embodiment, however, infrared radiation is evaluated instead or in addition. This makes it possible to detect a hot muffle, which comes, for example, from a preheating furnace and is positioned on the firing space bottom 46.

Compared with the muffle which has a temperature of, for instance, 600° C., the surrounding environment is distinctly colder, such that a particularly good differentiation is possible.

Figure 9:
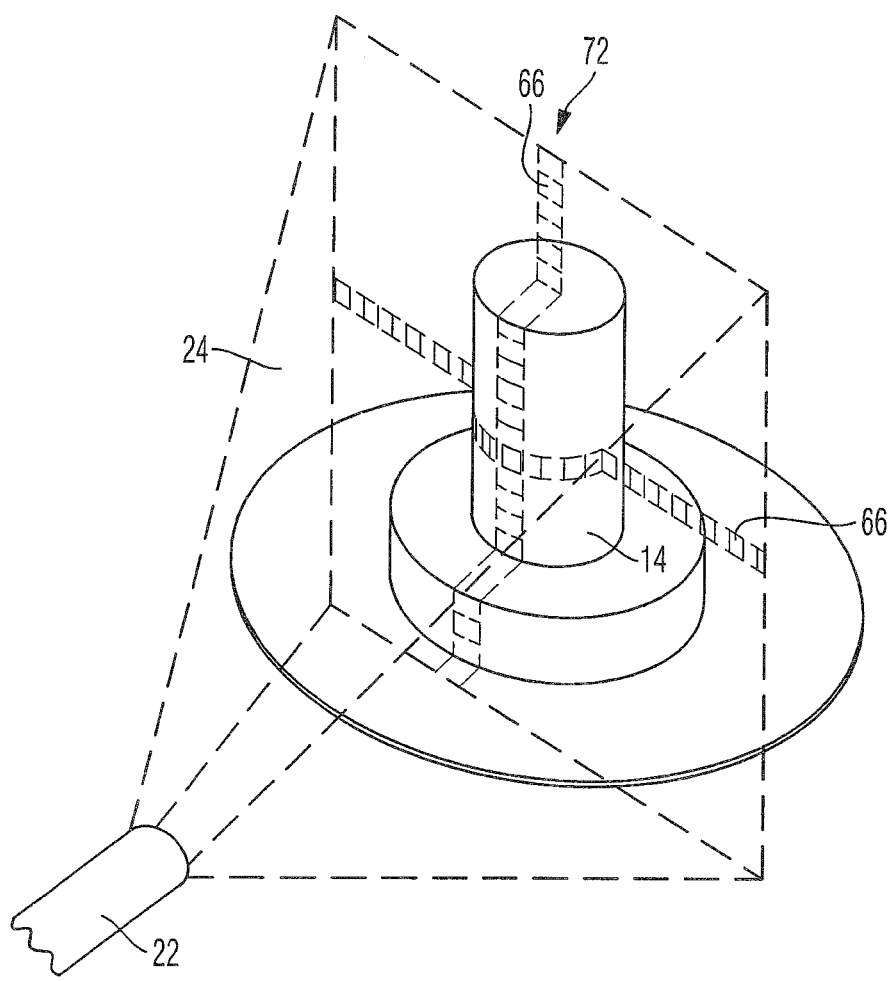
FIG. 9 is a schematic depiction of an optical sensor in accordance with the present invention, however in a modified embodiment.

The embodiment in accordance with FIG. 9 corresponds to the embodiment of FIG. 8, with, however, a horizontal detection position 72 being realized instead of the second vertical position. It is possible by detecting the corresponding pixels 66 to determine also the height of the muffle 14.

Figure 10:
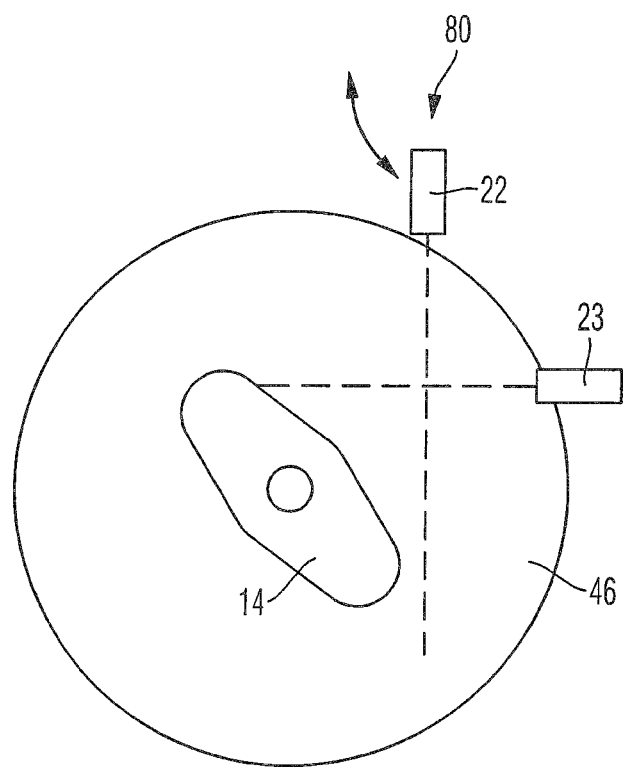
FIG. 10 is a schematic top view on a partially depicted further embodiment of a dental furnace in accordance with the present invention.

Also non-circular muffles can be detected, such as in the embodiment of the muffle 14 in accordance with FIG. 10. Also in this embodiment, two optical sensors 22 and 23 are employed, with one of the optical sensors being mounted in such a fashion that it can be swiveled around a vertical axis 80.

Figure 11:
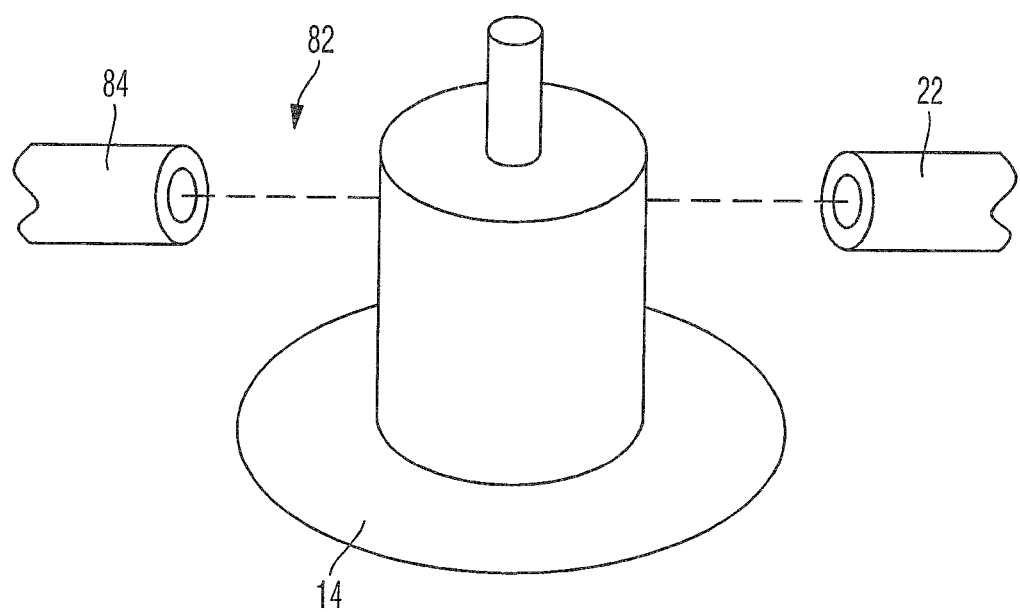
FIG. 11 is a schematic perspective view on a partially depicted further embodiment of a dental furnace in accordance with the present invention.

A detection of a size of the muffle via a light barrier 82 is provided in the embodiment in accordance with FIG. 11. The light barrier is provided with a transmitter 84 and the optical sensor 22 as a receiver. The light barrier 82 can, for example, remain stationary and then detect whether a muffle is introduced or not. Alternatively, it can also be moved in a horizontal direction, and with the help of the traveling way which is necessary in order for radiation emitted by the transmitter 84 to reach the optical sensor 22 again after coverage by the muffle 14, it is determined how large the diameter of the muffle is.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. Dental furnace for the firing operation of dental restorations comprising
   a furnace head and
   a firing space bottom which is suited to accommodate a dental restoration,
   wherein at least one optical sensor is arranged at the dental furnace or in its vicinity, the sensor comprises an output port connected to an evaluation device for evaluating at least one of the dental restoration, a muffle, a press plunger, and a firing charge carrier for at least one of dimensions, a shape and a position thereof,
   wherein the sensor is a thermal imaging camera having an infrared range of 3000 nm to 15,000 nm,
   wherein the sensor comprises a detection area which extends, at least partially, inside a firing space above the firing space bottom of the dental furnace,
   wherein the sensor is connected to a control device and is configured to directly detect a size and temperature of a dental restoration part or a muffle to be fired,
   wherein the control device determines furnace parameters depending on a size and temperature of the dental restoration part and/or muffle to be fired, and starts a program function for the firing of the dental restoration part and/or muffle based on the determined furnace parameters, and
   wherein there is no detection when the furnace is in a closed position.

2. Dental furnace in accordance with claim 1,
   wherein the evaluation device is connected to a display device, a control device, or both a display device and a control device,
   wherein the display device can display at least one of the dimensions, the shape and the position, and
   wherein the control device controls the dental furnace.

3. Dental furnace in accordance with claim 1,
   wherein a monitoring device of the dental furnace is connected to the sensor,
   wherein the monitoring device can detect a temporal change in the dimensions and/or the shape and/or the position.

4. Dental furnace in accordance with claim 1,
   wherein the furnace head is removable from the firing space and
   wherein the sensor is directed towards a detection area which extends between the firing space bottom and the furnace head in an open state of the furnace.

5. Dental furnace in accordance with claim 1,
   wherein the furnace head can be lifted off the firing space.

6. Dental furnace in accordance with claim 1,
   wherein the sensor is mounted so that it can be swiveled.

7. Dental furnace in accordance with claim 1,
   wherein the sensor is attached to the dental furnace so that it can be swiveled.

8. Dental furnace in accordance with claim 1,
   wherein the sensor comprises a picture recording device wherein an image of at least one of the dental restoration, the muffle, the press plunger, and the firing charge carrier can be recorded.

9. Dental furnace in accordance with claim 1,
   wherein the sensor comprises a picture recording device that evaluates a recorded image,
   wherein the recorded image comprises an object and a background,
   the picture recording device evaluates the recorded image at least line-wise, column-wise, or both, and determines the dimensions of the recorded image based on an evaluation result in a width extending in a parallel fashion to the firing space bottom or in a height extending in a vertical fashion to the firing space bottom of one or more of the dental restoration part, the muffle, the press plunger, and the firing charge carrier, by determining a number of pixels which correspond to the width or height, respectively, of the image recorded, from pixels corresponding to the object as opposed to pixels corresponding to the background, based on a pre-set criteria.

10. Dental furnace in accordance with claim 9,
wherein the criteria comprise one or more of a temperature, a brightness and a color of the object.

11. Dental furnace in accordance with claim 1,
wherein the sensor detects electromagnetic waves within a range of wavelengths of 380 nm and 18 µm and comprises a multitude of sensor elements.

12. Dental furnace in accordance with claim 1,
wherein the optical sensor comprises at least two sensor elements which are positioned at an angle to one another and have detection areas which at least partly overlap each other.

13. Dental furnace in accordance with claim 1,
wherein the optical sensor forms part of a light barrier which comprises at least two sensor elements and at least one transmitter of electromagnetic rays, and
wherein a presence of the electromagnetic rays can be detected by the sensor elements.

14. Process for operating a dental furnace, which dental furnace comprises a furnace head and a firing space bottom adapted to accommodate a dental restoration,
wherein at least one optical sensor is a thermal imaging camera having an infrared range of 3000 nm to 15,000 nm and is positioned at the dental furnace or in a vicinity thereof,
wherein the sensor directly detects a size and temperature and records an image of at least one of the dental restoration, a muffle, a press plunger, and a firing charge carrier to be fired and forwards it to a control device, and
wherein the dental furnace is controlled and/or the image is displayed by the control device, and
wherein the control device starts a program function depending on the image recorded or a signal output by the sensor for the firing operation of the dental restoration, and
wherein there is no detection when the furnace is in closed position.

15. Process in accordance with claim 14,
wherein the control device comprises a pre-selection of processing programs of the dental furnace after the control device has recognized an object recorded.

16. Process in accordance with claim 15,
wherein the object recorded is a size of the muffle positioned upon the firing space bottom.

17. Process in accordance with one of claim 14,
wherein the temperature of at least one of the dental restoration part, the muffle, the press plunger, and the firing charge carrier can be detected by the sensor, and
wherein the control device controls the dental furnace depending on the temperature detected.

* * * * *